United States Patent
MacDonald et al.

(10) Patent No.: US 6,542,828 B2
(45) Date of Patent: Apr. 1, 2003

(54) METHOD FOR DETERMINING THE QUANTITIES OF ACIDS OR BASES IN COMPLEX COMPOSITIONS

(75) Inventors: Leo Spitz MacDonald, Petersburgh, NY (US); Himanshu Bachubhai Vakil, Niskayuna, NY (US); Edward Brittain Stokes, Schenectady, NY (US); D Sangeeta, Cincinnati, OH (US); Howard John Farr, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 151 days.

(21) Appl. No.: 09/771,604

(22) Filed: Jan. 30, 2001

(65) Prior Publication Data

US 2002/0143474 A1 Oct. 3, 2002

(51) Int. Cl.[7] .............................................. G01N 31/00
(52) U.S. Cl. .......................................... 702/25; 702/22
(58) Field of Search .............................. 702/25; 73/61; 134/10; 204/227; 436/518; 435/34; 423/531; 422/56

(56) References Cited

U.S. PATENT DOCUMENTS

| | | | |
|---|---|---|---|
| 4,481,808 A | * | 11/1984 | Sakata et al. ............... 73/61.47 |
| 4,738,747 A | * | 4/1988 | Panson ........................ 134/10 |
| 5,593,611 A | | 1/1997 | Czech |
| 5,643,474 A | | 7/1997 | Sangeeta |
| 5,875,092 A | | 2/1999 | Jow et al. |
| 6,025,715 A | | 2/2000 | King et al. |
| 6,428,683 B1 | * | 8/2002 | Jaworowski et al. ........ 204/227 |

OTHER PUBLICATIONS

Copending U.S. patent application Ser. No. 09/425,556, Sangeeta et al.

Copending U.S. patent application Ser. No. 09/303,755, Sangeeta et al.

* cited by examiner

*Primary Examiner*—John Barlow
*Assistant Examiner*—Tung S Lau
(74) *Attorney, Agent, or Firm*—Noreen C. Johnson; Philip D. Freedman

(57) ABSTRACT

A method for determining the concentration of at least one acid or base in a complex solution is described. Multiple physical property values are first measured for the solution. The physical properties can be defined in the form of a set of solution property equations. The measured physical property values are then inserted into the solution property equations. When the equations are simultaneously solved, the desired concentration of the acid or basic component can be determined.

31 Claims, 1 Drawing Sheet

METHOD FOR DETERMINING THE QUANTITIES OF ACIDS OR BASES IN COMPLEX COMPOSITIONS

BACKGROUND OF THE INVENTION

This invention relates generally to analytical techniques. More specifically, it is directed to methods for determining the levels of acids or bases in various compositions, e.g., stripping solutions.

Acid and basic solutions have many uses, e.g., degreasing, electroplating, semiconductor metallization, cleaning, bright-dipping, etching, catalysis, and the like. They are often used as stripping compositions, e.g., to strip a metal coating from a metallic or non-metallic substrate. As a specific example, aluminide and platinum aluminide coatings used to protect superalloy components sometimes need to be stripped from the superalloy surface, e.g., during coating repair. (Aluminide coatings are often "diffusion coatings", i.e., the aluminide material is diffused into the substrate surface).

Stripping compositions for aluminide coatings are often based on various acids or combinations of acids, e.g., hydrochloric acid, nitric acid, and phosphoric acid. Examples of these compositions are found in application Ser. No. 09/303,755 (D. Sangeeta et al), filed on May 3, 1999, and assigned to the assignee of the present invention. The compositions usually must exhibit a number of attributes, e.g., the ability to quickly remove the coating from the substrate; and to be effective at relatively low use temperatures. Usually, the compositions must also be capable of stripping the particular coating material (e.g., aluminide or platinum-aluminide), without attacking the base metal of the substrate. It should also be noted that the compositions sometimes must be selective in their ability to remove different coating materials.

Some of the very effective stripping compositions for aluminide-type materials contain specific mixtures of acids, along with various other ingredients. For example, one such composition contains methanesulfonic acid, hydrochloric acid, sodium hypophosphite, and water. Such a composition possesses the various attributes discussed above, e.g., removal of the desired coating without damaging the base metal.

Maximum effectiveness for such a composition is usually achieved when the components are maintained at fairly specific levels. If the stripping composition deviates from those levels, serious problems could occur—especially in a commercial, production-type setting. For example, the composition may not sufficiently remove all of the coating material. In some instances, use of the composition may remove the coating material, but may also cause pitting of the substrate surface. As a consequence, the time and expense involved with high scrap levels and process inefficiency can have severe economic ramifications.

Obviously, a composition can initially be prepared according to a desired formulation. However, the content of such a composition (e.g., a stripping bath) usually changes during its operation. For example, various bath components are consumed at different rates. Thus, monitoring the level of each component at regular intervals is critical to maintaining the composition within selected parameters.

It is a relatively easy task to determine the level of components in a "simple" composition, e.g., a stripping bath containing only one acid. For example, a titration technique can efficiently be used to determine the amount of acid present in the bath at any given time. If the amount is out of specification, the bath contents can readily be adjusted, e.g., by addition of more acid, dilution, addition of compensating base, and the like.

However, analysis is much more difficult in the case of a complex acidic composition, e.g., one containing combinations of acids. (The same is true for a complex caustic composition, as described below). Titration techniques will usually measure only the total acid level. Such a measurement is insufficient by itself, since an operator would not know which particular acid is out of specification. As alluded to earlier, the presence of each acid (and possibly the non-acid components) at a particular level is necessary to ensure selectivity in terms of what is removed and what is not removed from the substrate.

Therefore, new methods for analyzing the level of components in complex compositions would be welcome in the art. The methods should be capable of accurately measuring the quantity of each significant component in the composition. The methods should also be readily adaptable to a production system, e.g., a large-scale stripping operation for removing aluminide-type coatings. It would be very desirable if the new analytical techniques could be carried out without an excessive amount of additional expense, in terms of costly equipment and time-consuming procedures.

SUMMARY OF THE INVENTION

A primary embodiment of the present invention embraces a method for determining the concentration of at least one acid or base in a complex composition. As used herein, the term "complex composition" is meant to embrace compositions which contain at least one acid or at least one base, in addition to at least one other component, other than the solvent-medium (e.g., water). The compositions are usually "solutions", i.e., uniformly dispersed mixtures, and that term is sometimes used herein. As further described below, the complex solutions analyzed according to the present invention are often acid mixtures, i.e., including more than one acid. They can alternatively be caustic mixtures, which include one or more bases with other components. The method comprises the following steps:

(a) measuring at least a first physical property value for the solution and a second physical property value for the solution, wherein the first physical property and the second physical property can be respectively defined in the form of a first solution property equation and a second solution property equation, wherein each equation expresses the respective physical property as a function of the concentration of one of the acids or bases;

(b) inserting the measured physical property values into the respective solution property equations, wherein the equations each include at least two unknown quantities, one of which is the desired concentration of the acid or base (i.e., the concentration being determined by this method); and (c) solving the solution property equations simultaneously, so as to determine the desired concentration.

The physical properties are characteristic of the solutions being measured. They are usually selected from the group consisting of electrical conductivity, opacity, density, refractive index, electromagnetic wave transmission, electromagnetic wave absorption, fluidity, open potential of solution, sound velocity, and color.

The solution property equations are derived from measurements of physical properties in each solution. The property equations are then used to determine the concentration of the various components in the solutions. In preferred embodiments, each solution property equation is derived from a process comprising the following steps:

(I) preparing at least two standard compositions, designated as a first standard composition and a second standard composition, each of which contains components present in the solution, in selected amounts, wherein the concentration of each component in one of the standard compositions varies from that of the other standard composition, within a selected tolerance range;

(II) measuring first and second physical properties for each standard composition, to obtain first and second property values, respectively;

(III) incorporating a set of all first property values and their corresponding, varying concentrations into a regression analysis algorithm, to obtain the solution property equation for the first physical property; and incorporating a set of all second property values and their corresponding, varying concentrations into the regression analysis algorithm, to obtain the solution property equation for the second physical property. (The regression analysis is often performed with the aid of a computer). The selected tolerance range for each component is usually less than about 20% of the concentration of the component in the first standard composition. As described below, more than two standard compositions are often prepared, and designated as additional standard compositions.

The solution being analyzed can comprise a variety of acid or basic compositions. The acidic compositions often include one or more components such as sulfonic acid, hydrochloric acid, and phosphoric acid. The basic compositions often include water and a hydroxide base, such as sodium hydroxide.

As mentioned above and further described below, the solution is often a stripping composition for removing a coating from a metal substrate. For example, it can be used to remove an aluminide-based coating or a ceramic coating from the surfaces of a turbine engine component, e.g., one formed of a superalloy material.

The solution being analyzed according to this invention is often contained in an apparatus for removing coatings from metal-based substrates. As described below, the apparatus usually comprises a pressure vessel capable of containing the solution and the substrates while the substrates are treated in the solution; a storage tank for the solution; and at least one passageway between the storage tank and the pressure vessel, for carrying the solution therebetween.

Other details regarding the various embodiments of this invention are provided below.

DETAILED DESCRIPTION OF THE INVENTION

Figure 1:
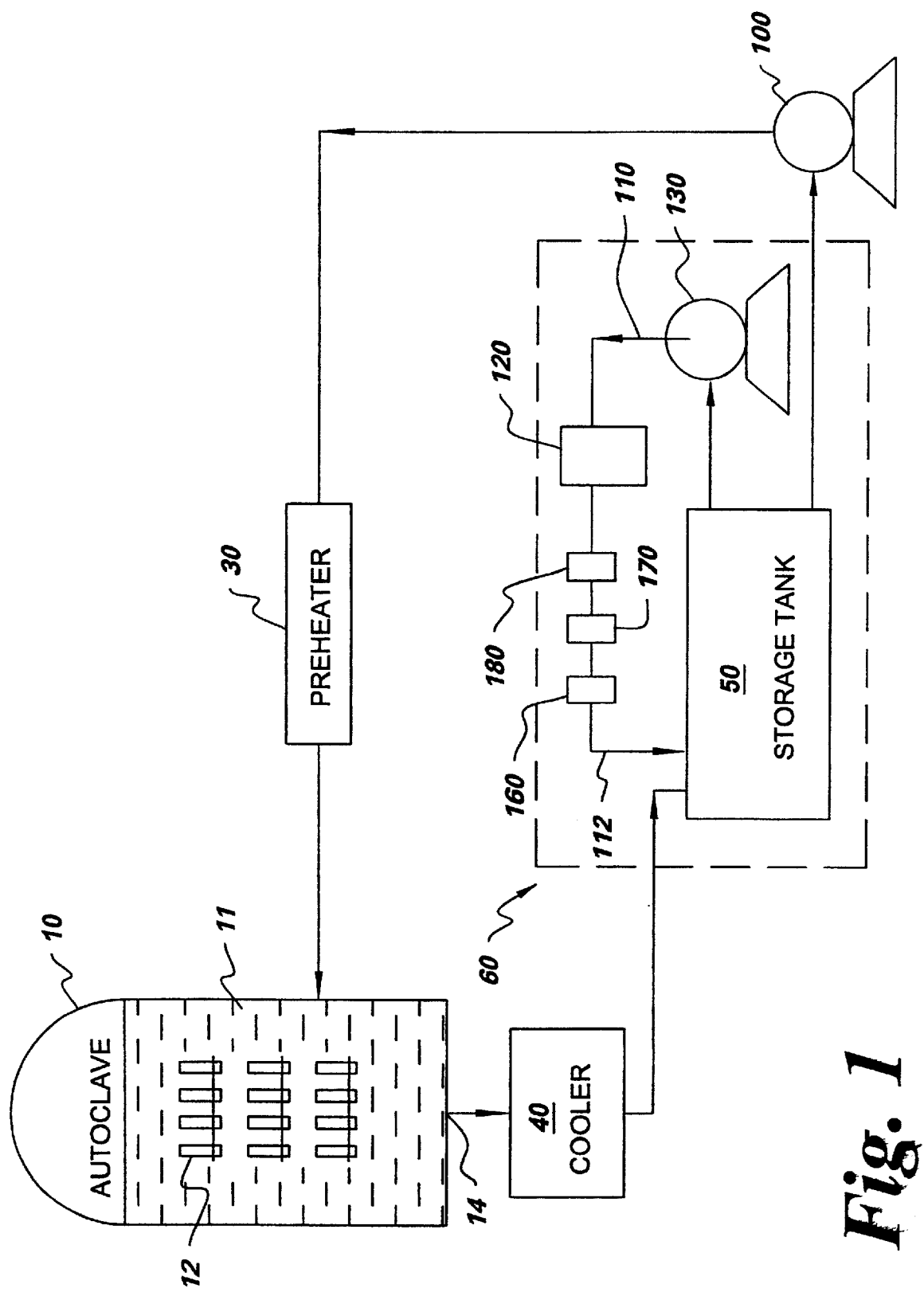
FIG. 1 is a schematic of an exemplary apparatus for removing coatings from substrates with a coating-removal solution, including an analysis system to measure the amount of selected acids or bases in the solution.

Any complex solution can be analyzed by the present invention. Specific examples of such solutions are provided below, e.g., stripping compositions for removing a variety of coatings from metal substrates, or from other coatings which are disposed over metal substrates. The acid solutions usually (but not always) contain about two to four acids, while the basic compositions usually contain one or two bases. The number and type of acids or bases will of course depend on the end use for the solution. The solution may also contain a wide variety of other additives. Non-limiting examples of these additives are inhibitors, dispersants, reducing agents, surfactants, chelating agents, wetting agents, deflocculants, stabilizers, anti-settling agents, anti-foam agents, and oxidizing agents.

As mentioned above, at least two physical property values are measured for the solution, e.g., first and second properties. The physical properties of the solution are related to the physical properties of the individual components in the solution. A number of physical properties can be used in the analysis of a solution. Non-limiting examples include electrical conductivity, opacity, density, refractive index, electromagnetic wave transmission, electromagnetic wave absorption, fluidity, open potential of solution, sound velocity, and color.

The selection of a particular physical property will depend primarily on several factors. The identity of the acids or bases, and their ability to exhibit a given property (e.g., conductivity or an electromagnetic property) in the solution is important. Moreover, the sensitivity of that property to changes in the concentrations of the components (i.e., its "range-of-response") is also very important. A change in the concentration of the acid or base of interest should result in a readily-measurable change in the quantity or other characteristic (e.g., a color change) of the physical property. For example, if a particular acid had a concentration which usually varied from about 35 to 45% by weight during the life of an end use solution, it would be preferable to select a physical property for the solution which changed over that concentration range. A more pronounced property change over a given concentration range permits the use of fewer data points to formulate solution property equations, and generally results in a more accurate mathematical model for solving the equations. A preferred group of physical properties for some embodiments is selected from the group consisting of electrical conductivity, density, and sound velocity.

Techniques for measuring each of the physical properties mentioned above are well-known in the art. As an example, electrical conductivity is usually determined by measuring the resistance of a solution through which a current is passed. Solution conductivity meters are often used. Density is often measured by the use of a mass flow meter. Sound velocity can be measured by a sound velocity meter, e.g., one utilizing a vibrating, acoustical probe. Color and opacity are typically measured by spectrophotometric techniques (some of which are referred to as "spectrocolorimetric" techniques). Moreover, electromagnetic wave transmission and absorption characteristics are also typically measured by the use of spectrophotometric techniques.

The refractive index of the solution can be measured by the use of a standard refractometer. Fluidity can be quantified by conventional techniques which measure the shear of a solution under an applied torque. Finally, the open potential can be measured by commercial devices, e.g., those which include a programmable power supply. In general, these devices apply a selected voltage (e.g., by scanning from one voltage to another), and then measure the corresponding current value of the half reaction-potential for the solution. (The concept of open potential is generally discussed in various references, such as U.S. Pat. No. 5,875,092, which is incorporated herein by reference).

Those of ordinary skill in the analytical arts are able to use other available techniques to measure the properties listed above. They are also able to modify techniques to be compatible with the particular solution being analyzed according to this invention. Moreover, many references which describe these techniques and other relevant procedures are available, such as *Quantitative Chemical Analysis*, by Daniel Harris, W.H. Freeman & Co., N.Y. 1999, 5th Edition; and *Fundamentals of Analytical Chemistry*, D. A. Skoog et al, 3rd edition, Holt; Rinehart and Wilson, 1976. Both references are incorporated herein by reference.

For many acidic and basic solutions, the most convenient physical properties to employ are some combination of electrical conductivity, density, and sound velocity. In the case of solutions which contain strong acids (such as methanesulfonic acid and hydrochloric acid), a combination of electrical conductivity and density is often preferred, in those situations where two unknown acid concentrations are to be determined.

The number of solution property equations employed in the method of this invention depends on the number of "independent" acids or bases being analyzed. As used herein, "independent" refers to acids or bases which are not related to any other component in the solution by a fixed ratio. (If the acid or base is related to another component by a fixed ratio, a separate solution property equation should not be necessary, assuming the quantity of the other component can be measured). In general, the number of solution property equations is equal to the number of properties being measured. Moreover, the number of independent acids or bases needs to be equaled or exceeded by the number of solution property equations.

As an example, if two independent acids are being measured according to the present invention, two solution property equations are usually required. If three independent acids are being measured, then three equations are usually needed. Thus, the measurement of two acids or bases requires two different physical property measurements, while the measurement of three acids or bases requires three different physical property measurements.

The derivation (formulation) of the solution property equations usually begins with the preparation of at least two standard compositions. Each of these compositions contains the components present in the solution which will eventually be analyzed. The concentration of each component varies from the concentration of the component in the other standard composition. The variation in concentration occurs over a selected tolerance range.

The size of the tolerance range can also vary. It is at least large enough to provide a measurable change in some measured physical property, when one of the standard compositions is compared with the other. At a minimum, the tolerance range usually extends, in a positive or negative direction, from a desired composition (e.g., a starting composition) to an expected, modified composition.

To illustrate, a desired composition for removing various coatings from metal surfaces may contain selected amounts of several acids, along with selected amounts of water and other components, such as phosphite reducing agents. After such a composition is in use for a period of time, some of the individual components often become depleted. For example, the concentration of one of the acids may significantly decrease as the process is carried out, resulting in a "modified" composition. (In some instances, the concentration of one or more of the acids may significantly increase, due to a loss of water from the composition, for example. This phenomenon can occur simultaneously with depletion of one or more of the acids). Typically, the selected tolerance range is less than about 20% of the concentration of the component in the starting composition. However, the optimum range will depend in part on the physical property measurements obtained for the compositions, and on the ability to generate useful solution property equations, as described below.

In practice, more than two standard compositions are usually prepared. All of the compositions would contain the same components, but at different levels within (or just outside) the tolerance range. A larger number of compositions which are measured for selected physical properties results in the generation of a larger number of data points. In general, a greater number of data points permit the generation of more precise solution property equations. As a result, smaller changes in the acid or base concentrations in a monitored solution can often be detected. (However, it is not always necessary to detect very small changes in the concentration of a component). Usually, the total number of standard compositions prepared is at least about two times the number of acids or bases which have undetermined concentrations. In some preferred embodiments, the total number of standard compositions prepared is at least about three times the number of acids or bases which have undetermined concentrations.

As mentioned above, at least two physical properties are then measured for each standard composition. A set of data points (i.e., "property values") is thereby obtained for each physical property. For example, if 12 standard compositions are employed, 12 data points would be obtained for conductivity, and 12 data points would be obtained for density. Sometimes, the data points may not exhibit a "spread" which would be sufficient for generating a meaningful solution property equation. In those instances, more data could be obtained by preparing additional, standard compositions, having a wider range of component concentrations. Alternatively, one could select a different physical property which would provide the desired data point spread.

The data points for the first physical property and the corresponding concentrations for each component are then incorporated into an algorithm which minimizes a function of two variables. This type of algorithm is well known in the art, and is often referred to as a "regression analysis algorithm". A specific technique of this type is known as the "method of least squares", which is described in many references. Examples include: *Encyclopedia Americana*, Volume 17, Grolier, Inc., (1981), p. 123 et seq., and *Calculus and Analytical Geometry*, Alternate Edition, G. Thomas, Jr., Addison-Wesley, Inc., 1972, p. 716 et seq. Other texts which deal with related topics are also available. For example, the determination of solutions for simultaneous equations with two or more variables is explained in *Encyclopedia Americana*, Volume 10, Grolier, Inc., (1981), p. 530 et seq. An example of a commercially available computer software program for regression analysis is the Minitab™ program, available from Minitab, Inc., State College, Pa. Its use is described in many references, such as U.S. Pat. Nos. 6,025,715 and 5,593,611, which are incorporated herein by reference.

An exhaustive description of the method of least squares is not necessary. In general terms, it involves the fitting of a straight line $$y = mx + b \qquad (I)$$

to a set of experimentally observed points $(x_1, y_1), (x_2, y_2), \ldots, (x_n, y_n)$, where y can be the observed value of a physical property, i.e., its quantity, at a given concentration x for one of the components. As explained in the G.

Thompson text, the above equation can be used to express a set of "deviations". These deviations represent the cumulative sum of the differences between "observed" values for y, and the value for y which is predicted by the straight-line equation set forth above, when observed values for x are inserted. In brief, the straight line which comes closest to fitting all of the observed values (or "data points") is one in which the value of the square of all of the negative and positive deviations from the line is a minimum.

As an illustration, an expansion of equation I can be described, for an exemplary composition which contains three soluble components, e.g., water ($H_2O$), a first acid, and a second acid. The concentrations and physical property values for the standard compositions can be inserted into the appropriate regression analysis program, generating the following equation:

$$y=(m_1)[\text{acid 1}]+(m_2)[\text{acid 2}]+(m_3)[H_2O]+b \quad \text{(II)},$$

where the brackets represent the concentrations of each component. (In other words, this format would involve solving a series of these equations, each with different data points corresponding to the different standard compositions which include acid 1 and acid 2.)

As mentioned above, this type of regression analysis algorithm can very conveniently be implemented by using a computer. A variety of commercially-available software programs are designed to accept a series of data points based on two or more variables, as in the present case. The example which follows provides a general illustration for the application of such a program to sample compositions.

The use of the regression analysis algorithm results in the generation of the solution property equations. In the case of a solution in which the concentration of two components is to be determined, two solution property equations would be generated. In simplified form for an exemplary, acid-containing solution, the equations are as follows:

$$y_{p1}=(m_1)[\text{acid 1}]+(m_2)[\text{acid 2}]+(m_3)[H_2O]+b_1 \quad \text{(III)},$$

and $$y_{p2}=(m_4)[\text{acid 1}]+(m_5)[\text{acid 2}]+(m_6)[H_2O]+b_2 \quad \text{(IV)}$$

For these equations, "$y_{p1}$" is the quantity of the first physical property, and "$y_{p2}$" is the quantity of the second physical property. All of the slope values $m_1$ through $m_6$ are derived from the regression analysis, as are values for $b_1$ and $b_2$. Moreover, the water concentration for each equation can effectively be canceled out, as water can be expressed as the remainder-portion after one accounts for the two acid concentrations. Thus, when $y_{p1}$ and $y_{p2}$ are measured for a solution with unknown amounts of the acids, the two, remaining unknown values in the equations are acid 1 and acid 2. Those two values are readily determined when the two equations are solved simultaneously. (The last step can also be done with the use of a computer or scientific calculator.) Moreover, the concentrations of various bases in a caustic solution can be determined in analogous fashion. In such a case, equations III and IV would represent solution property equations generated by the variation of basic concentrations (and other soluble ingredients), after the appropriate physical property values have been measured.

As alluded to earlier, a variety of solutions can be analyzed according to the present invention. As an example, acidic mixtures often (but not always) comprise at least one acid selected from the group consisting of halide acids such as hydrochloric acid; oxy-halide acids such as perchloric acid; an aliphatic sulfonic acid; an aromatic sulfonic acid, sulfuric acid, phosphoric acid, perchloric acid, and nitric acid. Various combinations of these acids are also possible. Sulfonic acids are often used when the solution is a stripping composition for removing aluminide-type materials from a metal substrate, e.g. a superalloy substrate. Examples of sulfonic acids include methanesulfonic acid, ethanesulfonic acid, benzene sulfonic acid, toluene sulfonic acid, and naphthalene sulfonic acid.

Some of the stripping compositions for removing aluminide compounds include a sulfonic acid in combination with an inorganic acid, such as hydrochloric acid, nitric acid, or perchloric acid. They also sometimes include phosphoric acid or a derivative thereof, e.g., a phosphite compound such as sodium hypophosphite. Suitable compositions of this type are generally described in the above referenced patent application Ser. No. 09/303,755, which is incorporated herein by reference.

As mentioned previously, a variety of caustic solutions can be analyzed by this invention. Some of them are described in U.S. Pat. No. 5,643,474 (D. Sangeeta), which is incorporated herein by reference. These solutions may comprise a mixture of water and a basic compound (inorganic or organic), such as a hydroxide base. Non-limiting examples of the basic compounds include sodium hydroxide, potassium hydroxide, ammonium hydroxide, tetramethylammonium hydroxide, and lithium hydroxide. Mixtures which comprise two or more of such compounds are sometimes utilized. Various other additives which reduce surface tension may also be present in the caustic solution, such as conventional surfactants, chelates, and wetting agents. Sometimes, the caustic solution further includes an organic compound (i.e., an additional organic compound in the case of a solution which already includes an organic basic compound). Non-limiting examples of the organic compounds include alcohols such as methanol, ethanol, propanol, and isopropyl alcohol; as well other compounds, such as acetone, liquid carbon dioxide, or liquid ammonia. Mixtures of two or more of any of these compounds can also be used. The proportions of the various ingredients for the caustic solution will of course depend on its end use.

Caustic solutions are often employed to remove ceramic coatings from coated metal parts, without damaging the substrate or any intervening coating. As described in the referenced U.S. Pat. No. 5,643,474, some of the caustic solutions are very effective at removing physical vapor-deposited or air plasma-sprayed thermal barrier coatings (TBC's) from a superalloy substrate. These coatings are often based on chemically stabilized zirconia, and the solutions are typically utilized within an autoclave. Removal of the TBC occurs without damage to the substrate, or to an underlying bond coat (e.g., an aluminide-type material).

One apparatus and process for removing coatings from metal substrates is described in the commonly owned patent application designated as Ser. No. 09/425,556 (D. Sangeeta et al). This application was filed on Oct. 22, 1999, and is incorporated herein by reference. The details regarding such an apparatus can be found in the specification for this application. In brief, the metal substrates (e.g., turbine engine airfoils), are treated in a pressure vessel, such as an autoclave, which contains a caustic solution. The concentration of the bases in the solution can be measured within or between various elements of such an apparatus. After measurement according to the present invention, adjustments to the solution can then be made to bring it back into specification. For example, additional base can be added if a particular basic component were depleted. (A portion of the solution can be discarded and replaced with fresh solution, as well).

If a basic component were found to be in excess, various conventional techniques to correct the composition can also be undertaken. For example, a portion of the solution can be drained, and/or a neutralizing agent can be added to compensate for the excess base. Alternatively, additional water can be added to further dilute the solution. As another alternative, a portion of the basic component can be crystallized and then filtered out of the solution.

As described in Ser. No. 09/425,556, the analytical devices for carrying out the method of this invention can be incorporated into a filtering loop. For example, a filter within the autoclave could serve to remove large particles from the coating-removal solution ("reagent"), before it is directed out of the autoclave and into a circulation loop. The circulation loop may include a storage tank for the reagent, and a pre-heater for raising the temperature of the reagent before it re-enters the autoclave. Other features may also be included, e.g., an additional filter.

FIG. 1 depicts an exemplary apparatus for removing coatings from substrates. (The figure is very similar to FIG. 3 of Ser. No. 09/425,556, and represents one, non-limiting example of the various systems depicted in FIGS. 1–8 of that disclosure). The apparatus includes a pressure vessel 10 (such as an autoclave), which contains the reagent 11. Metal substrates 12 are positioned within the autoclave, so that they can be treated with the reagent. When the reagent is to be re-circulated for any reason (e.g., further filtration and/or adjustment of composition), it can be directed out of pressure vessel 10 through exit 14. It may then be directed into cooler means 40 for storage in tank 50.

Attached to storage tank 50 is an illustrative filtration circulation loop 60 that includes a pipe 110 that provides communication for the reagent from pump 130, through a filter 120. The reagent then passes through a series of analytical devices, which measure two or more of the physical properties described previously. In this illustration, the analytical devices are depicted as elements 160, 170, and 180 of the filtration loop. They do not have to be part of this loop. For example, they could be connected to the overall treatment system at any location suitable for sampling the reagent, and they may be connected as an independent loop. However, it is often preferable to locate the devices adjacent storage tank 50, so that the reagent can be readily adjusted if the physical properties (e.g., acid or base levels) are found to vary outside of acceptable ranges. Moreover, it is usually preferable to locate the analytical devices downstream from filter 120. This placement ensures that the measurements are unaffected by suspended solids in the reagent.

As explained previously, analytical devices 160, 170, and 180 represent measuring systems for various physical properties of the reagent. For example, device 160 can measure electrical conductivity; device 170 can measure density; and device 180 can measure sound velocity. When only two physical properties are being measured, only two devices need to be activated (or installed). If, for example, four physical properties needed to be measured, a fourth device could be readily installed.

As described in Ser. No. 09/425,556, it is sometimes desirable if two of the measured physical properties respond in an inverse manner (e.g., "orthogonally"). For example, in the case of a caustic solution, sound velocity may decrease with increasing sodium hydroxide content. Density, however, may rise at the same time. In that instance, changes in these properties can very accurately be measured, and linked to changes in the chemistry of the reagent.

Pipe 112 (i.e., the extension or continuation of pipe 110) carries the analyzed reagent back to storage tank 50. As mentioned previously, the content of the reagent can be adjusted to bring it back into proper specification, based on the results of the analytical tests. A pump 100 can then transfer the reagent back to pressure vessel 10. Usually, the reagent is first passed through pre-heater 30, to bring it up to a desired, elevated temperature for use.

As described in Ser. No. 09/425,556, additional equipment for measuring physical properties can be added or substituted for the equipment depicted in the various embodiments. For example, probes capable of measuring other properties can be added as needed. The probes can be attached to read-outs (not shown) that can permit continuous monitoring, or periodic sampling of the particular properties. The read-outs can be analog or digital, and may be connected to a digital device, such as a computer. Moreover, various arrangements for monitoring the reagent can be used. For example, the measured values can be stored (e.g., electronically) for later analysis. Alternatively, warning alerts can be emitted in some manner, if acceptable limits for the levels of the various components are exceeded.

EXAMPLES

The practice of this invention is illustrated, but not limited, by the example provided below. Unless otherwise noted, all parts or percents are by weight.

A mixture of methanesulfonic acid (MSA), hydrochloric acid (38° baume) (HCl), sodium hypophosphite (NaH$_2$PO$_2$) and water (40:10:2:48 by weight, respectively) was employed as a nominal composition. (Such a composition was disclosed in the above-referenced patent application, Ser. No. 09/303,755). The components were varied to provide ten total compositions. The variation for the components was within the following ranges: MSA: 36–43 wt %; HCl: 4–15 wt %; NaH$_2$PO$_2$:1–7 wt %; and water: 44–52 wt %. The ten compositions provided a set of ten data points from the conductivity meter, mass flow meter (density), and sound velocity meter.

The components were varied a second time, according to the following ranges: MSA: 37.5–40.5 wt %; HCl: 9–15 wt %; NaH$_2$PO$_2$:0.2–1.5 wt %; and water: 46–49.5 wt %. This series resulted in 15 data points, using just the conductivity meter and the mass flow meter. (For these compositions, the sound velocity measurements were not sensitive to the small changes in solution chemistry).

The components were varied a final time, and in this instance, the concentration of MSA was varied at two widely different ranges. For one set of compositions, the ranges were as follows: MSA: 50–54 wt %; and water: 34–36 wt %. In that instance, the HCl range was from 9–15 wt %, and the NaH$_2$PO$_2$ range was from 0.2–1.5 wt %. For another set of compositions, the MSA range was from 25–27 wt %, and the water range was from 58–64 wt %, while the HCl and NaH$_2$PO$_2$ ranges remained the same, i.e., 9–15 wt % and 0.2–1.5 wt %, respectively. These two sets of compositions generated 8 additional data points from the conductivity and mass flow meters.

Based on this set of data, the equations V and VI were generated, using a regression analysis carried out with the Minitab™ program. (The terms of the equation were adjusted to account for the fixed ratio of water to MSA, which allowed for removal of water as a separate term):

$$\text{Conductivity} = -7558 + 362193(1/[\text{MSA}]) - 105([\text{HCl}]) - 113(100 - [\text{HCl}] - ([\text{MSA}]/0.45)) \quad (V)$$

and $$\text{Density} = 17.1664 - 0.192([\text{MSA}]) - 0.160([\text{HCl}]) - 0.156(100 - [\text{HCl}] - ([\text{MSA}]/0.45)) - 0.133([\text{MSA}]/0.45 - [\text{MSA}]) \quad (VI)$$

Conductivity and density measurements are then taken for a given solution having unknown quantities of MSA and HCl. The values are inserted into the two equations. The equations are then solved simultaneously by standard algebraic techniques, e.g., substitution of the values, or the use of matrices. The solution to the equations results in the determination of the concentration of each component, in weight percent.

In regard to describing the present invention, it is not necessary to set forth all of the individual data calculations used in a Minitab™ analysis. The following section simply provides a brief description of the analysis for one set of data points, based on conductivity measurements.

Conductivity Analysis

| | | | | Regression Analysis[a] | | |
|---|---|---|---|---|---|---|
| MSA | $H_2O$ | HCl | $NaH_2PO_2$ | Conductivity | $MSA^{-1}$ | COEF1[b] |
| 44.000 | 36.000 | 13.00 | 7.00 | 275 | 0.0227273 | [c] |
| 44.000 | 36.000 | 15.00 | 5.00 | 286 | 0.0227273 | [d] |
| 46.200 | 37.800 | 15.00 | 1.00 | 324 | 0.0216450 | [e] |
| 46.475 | 38.025 | 8.50 | 7.00 | 260 | 0.0215169 | [f] |
| 47.080 | 38.520 | 10.20 | 4.20 | 297 | 0.0212404 | — |
| 48.400 | 39.600 | 7.00 | 5.00 | 291 | 0.0206612 | — |
| 48.950 | 40.050 | 4.00 | 7.00 | 291 | 0.0204290 | — |
| 49.225 | 40.275 | 9.50 | 1.00 | 355 | 0.0203149 | — |
| 50.600 | 41.400 | 4.00 | 4.00 | 337 | 0.0197628 | — |
| 52.250 | 42.750 | 4.00 | 1.00 | 374 | 0.0191388 | — |

[a] MSA, $H_2O$, HCl, and $NaH_2PO_2$ are expressed as weight-concentrations.
[b] "COEF1" = slope value for each equation, e.g., the "m" value of equation I.
[c] = −1687.9081419155
[d] = −31.6480152712
[e] = −41.2850977858
[f] = 16889.7148070164

The regression equation generated by the computer program, along with additional statistical data, is as follows:

Conductivity=−937+24.2[MSA]+10.0[HCl]

| Predictor | Coef | StDev | "T"* | "P"** |
|---|---|---|---|---|
| Constant | −937.5 | 151.4 | −6.19 | 0.000 |
| [MSA] | 24.223 | 2.876 | 8.42 | 0.000 |
| [HCl] | 10.044 | 1.784 | 5.63 | 0.001 |

*standard statistical term, i.e., measurement at one standard deviation for the probability of a random event;
**standard statistical term, i.e., probability of a random event (up to 99% standard deviation).

Note: Other satistical measurements conventional in the art were determined in this instance to be as follows:

"S"=11.78

"R-Sq"=92.1%

"R-Sq(adj)"=89.8%

Additional regression analysis was performed on all of the other data sets, corresponding to density and conductivity, to generate analogous solution property equations. As stated above, other programs are available for carrying out a regression analysis, once the appropriate physical data has been obtained. As an alternative to using the "squared" values in a least squares method, absolute values are sometimes used.

Having described preferred embodiments of the present invention, alternative embodiments may become apparent to those skilled in the art, without departing from the spirit of this invention. Accordingly, it is understood that the scope of this invention is to be limited only by the appended claims.

What is claimed:

1. A method for determining the concentration of at least one acid or base in a complex solution, comprising the following steps:

(a) measuring at least a first physical property value for the solution and a second physical property value for the solution, wherein the first physical property and the second physical property can be respectively defined in the form of a first solution property equation and a second solution property equation, wherein each equation expresses the respective physical property as a function of the concentration of one of the acids or bases;

(b) inserting the measured physical property values into the respective solution property equations, wherein the equations each include at least two unknown quantities, one of which is the desired concentration of the acid or base; and (c) solving the solution property equations simultaneously, so as to determine the desired concentration of the acid or base;

wherein a first physical property is selected from the group consisting of electrical conductivity, opacity, density, refractive index, electromagnetic wave transmission, electromagnetic wave absorption, fluidity, open potential of solution, sound velocity, and color; and the second physical property is selected from the group consisting of electrical conductivity, opacity, density, refractive index, electromagnetic wave transmission, electromagnetic wave absorption, fluidity, open potential of solution, sound velocity, and color.

2. The method of claim 1, wherein the first physical property and the second physical property are selected from the group consisting of electrical conductivity, density, and sound velocity.

3. The method of claim 1, wherein each solution property equation is derived from a process comprising the following steps:

(I) preparing at least two standard compositions, designated as a first standard composition and a second standard composition, each of which contains components present in the solution, in selected amounts, wherein the concentration of each component in one of the standard compositions varies from that of the other standard composition, within a selected tolerance range;

(II) measuring first and second physical properties for each standard composition, to obtain first and second property values, respectively;

(III) incorporating a set of all first property values and their corresponding, varying concentrations into a regression analysis algorithm, to obtain the solution property equation for the first physical property; and incorporating a set of all second property values and their corresponding, varying concentrations into the regression analysis algorithm, to obtain the solution property equation for the second physical property.

4. The method of claim 3, wherein the selected tolerance range for each component is less than about 20% of the concentration of the component in the first standard composition.

5. The method of claim 3, wherein the selected concentrations for the first standard composition represent the desired concentrations for the components in the solution, and the selected concentrations of components for the second standard composition represent the approximate, modified concentrations expected for the components after the solution has been in use; wherein the difference between the concentrations in the first standard composition and those in the second standard composition represents the selected tolerance range.

6. The method of claim 3, wherein more than two standard compositions are prepared, as additional standard compositions.

7. The method of claim 6, wherein each of the additional standard compositions contains component concentrations which are substantially within the selected tolerance range.

8. The method of claim 6, wherein the total number of standard compositions prepared is at least about two times the number of acids or bases which have undetermined concentrations.

9. The method of claim 8, wherein the total number of standard compositions prepared is at least about three times the number of acids or bases which have undetermined concentrations.

10. The method of claim 3, wherein the regression analysis algorithm is based on the least squares computational method.

11. The method of claim 3, wherein the regression analysis algorithm is implemented with the use of a computer.

12. The method of claim 1, wherein the solution is an acidic mixture comprising at least one acid selected from the group consisting of halide acids; oxy-halide acids; an aliphatic sulfonic acid; an aromatic sulfonic acid, sulfuric acid, phosphoric acid, perchloric acid, nitric acid, and mixtures thereof.

13. The method of claim 1, wherein the solution is an acidic mixture comprising at least one aliphatic or aromatic sulfonic acid.

14. The method of claim 13, wherein the sulfonic acid is selected from the group consisting of methanesulfonic acid, ethanesulfonic acid, benzene sulfonic acid, toluene sulfonic acid, and naphthalene sulfonic acid.

15. The method of claim 14, wherein the solution further comprises an inorganic acid.

16. The method of claim 15, wherein the inorganic acid is selected from the group consisting of hydrochloric acid, nitric acid, and perchloric acid.

17. The method of claim 13, wherein the solution further comprises phosphoric acid derivative thereof.

18. The method of claim 1, wherein the solution is a composition for selectively removing an aluminide-containing coating from the surface of a metal-based substrate.

19. The method of claim 18, wherein the solution comprises at least one aliphatic or aromatic sulfonic acid; an inorganic acid, and phosphoric acid or a derivative thereof.

20. The method of claim 18, wherein the metal-based substrate is a turbine engine component.

21. The method of claim 18, wherein the metal-based substrate comprises a superalloy material.

22. The method of claim 1, wherein the solution is a caustic composition suitable for removing ceramic coat from the surfaces of articles.

23. The method of claim 22, wherein the caustic composition is suitable for removing the ceramic coatings while leaving an underlying coating intact.

24. The method of claim 22, wherein the caustic composition comprises a base and water.

25. The method of claim 1, wherein the solution is contained in an apparatus for removing coatings from metal-based substrates.

26. The method of claim 25, wherein the apparatus comprises:
   (i) a pressure vessel capable of containing the solution and the substrates while the substrates are treated in the solution;
   (ii) a storage tank for containing the solution when it is not being used to treat the substrates; and
   (iii) at least one passageway between the storage tank and the pressure vessel, for carrying the solution therebetween,
wherein the method is carried out in a location in the passageway.

27. The method of claim 25, wherein the apparatus comprises:
   (I) a pressure vessel capable of containing the solution and the substrates while the substrates are treated in the solution;
   (II) a storage tank for containing the solution when it is not being used to treat the substrates; and
   (III) a circulation loop which comprises a circulation pump and at least one filter, to circulate the solution from the storage tank, through the filter, and back into the storage tank;
wherein analysis equipment for determining the concentration of the acid or base is located within the circulation loop.

28. A method for determining the concentration of at least one acid in a stripping solution for removing metallic or ceramic coatings from superalloy substrates, wherein the stripping solution comprises a mixture of acids, said method comprising the following steps:
   (a) measuring at least a first physical property value for the solution and a second physical property value for the solution, wherein the first physical property and the second physical property can be respectively defined in the form of a first solution property equation and a second solution property equation, wherein each equation expresses the respective physical property as a function of the concentration of one of the acids;
   (b) inserting the measured physical property values into the respective solution property equations, wherein the equations each include at least two unknown quantities, one of which is the desired concentration of the acid; and
   (c) solving the solution property equations simultaneously, so as to determine the desired concentration;
wherein the mixture of acids comprises at least two acids selected from the group consisting of halide acids; oxy-halide acids; an aliphatic sulfonic acid; an aromatic sulfonic acid, sulfuric acid, phosphoric acid, perchloric acid, and nitric acid.

29. The method of claim 28, wherein the superalloy substrate is a component of a turbine engine, and the metallic coating comprises aluminide or platinum-aluminide.

30. The method of claim 28, wherein the mixture of acids further includes water and a phosphite reducing agent.

31. A method for determining the concentration of a base in a caustic stripping solution for removing metallic or ceramic coatings from superalloy substrates, wherein the stripping solution comprises an organic compound, a base, and water, wherein the organic compound is selected from the group consisting of methanol, ethanol, propanol, isopropyl alcohol, acetone, liquid carbon dioxide, liquid ammonia, and mixtures thereof and the base is selected from the group consisting of sodium hydroxide, potassium hydroxide, ammonium hydroxide, said method comprising the following steps:

(a) measuring at least a first physical property value for the solution and a second physical property value for the solution, wherein the first physical property and the second physical property can be respectively defined in the form of a first solution property equation and a second solution property equation, wherein each equation expresses the respective physical property as a function of the concentration of one of the bases;

(b) inserting the measured physical property values into the respective solution property equations, wherein the equations each include at least two unknown quantities, one of which is the desired concentration of the base; and (c) solving the solution property equations simultaneously, so as to determine the desired concentration of the base;

wherein the superalloy substrate is a component of a turbine engine, and the ceramic coating comprises chemically stabilized zirconia.

* * * * *